United States Patent [19]

Cannon

[11] Patent Number: 5,423,775
[45] Date of Patent: Jun. 13, 1995

[54] LOCKING CONNECTOR ASSEMBLY

[75] Inventor: Raymond E. Cannon, Poway, Calif.

[73] Assignee: Winfield Industries, San Diego, Calif.

[21] Appl. No.: 184,682

[22] Filed: Jan. 21, 1994

[51] Int. Cl.⁶ .................................................. A61M 25/00
[52] U.S. Cl. .................................. 604/283; 604/905; 285/305
[58] Field of Search ............... 604/283, 284, 905; 285/80–82, 260, 283, 305, 308, 309

[56] References Cited

U.S. PATENT DOCUMENTS

| | | |
|---|---|---|
| 3,976,073 | 8/1976 | Quick . |
| 3,986,508 | 10/1976 | Barrington . |
| 4,005,710 | 2/1977 | Zeddies . |
| 4,149,535 | 4/1979 | Volder . |
| 4,306,705 | 12/1981 | Svensson . |
| 4,338,933 | 7/1982 | Bayard . |
| 4,362,156 | 12/1982 | Feller . |
| 4,405,163 | 9/1983 | Voges . |
| 4,433,973 | 2/1984 | Kurtz . |
| 4,457,749 | 7/1984 | Bellotti . |
| 4,511,359 | 4/1985 | Vaillancourt . |
| 4,752,292 | 6/1988 | Lopez . |
| 4,834,716 | 5/1989 | Ogle . |
| 4,878,897 | 11/1989 | Katzin . |
| 4,920,970 | 5/1990 | Wyatt . |
| 5,000,614 | 3/1991 | Walker et al. ............... 403/326 |
| 5,040,831 | 8/1991 | Lewis ............................ 285/305 |
| 5,120,324 | 6/1992 | Sancoff ......................... 604/283 |
| 5,152,555 | 10/1992 | Szabo ............................ 285/93 |
| 5,195,964 | 3/1993 | Kletzky . |
| 5,199,947 | 4/1993 | Lopez . |
| 5,248,306 | 9/1993 | Clark et al. ................... 604/283 |
| 5,290,222 | 3/1994 | Feng et al. ..................... 604/86 |
| 5,356,396 | 10/1994 | Wyatt et al. ................... 604/283 |

FOREIGN PATENT DOCUMENTS

| | | | |
|---|---|---|---|
| 855319 | 11/1952 | Germany . | |
| 9219314 | 11/1992 | WIPO ........................... | 604/283 |

Primary Examiner—Corrine Maglione
Attorney, Agent, or Firm—Nydegger & Associates

[57] ABSTRACT

A locking connector assembly is provided for use with Y-sites and/or other infusion line fittings. The connector assembly includes a shrouded connector including a cannula. A retention clip having a pair of prongs is provided. When the shrouded connector is installed on a Y-site or other fitting, and the retention clip is in the locking configuration, the prongs of the retention clip extend through a pair of opposing through-slots in the shroud to cooperatively engage a surface irregularity on the Y-site or other fitting thereby preventing disengagement of the shrouded connector from the Y-site or other fitting.

23 Claims, 5 Drawing Sheets

LOCKING CONNECTOR ASSEMBLY

FIELD OF THE INVENTION

The present inventions pertains to a device used to connect and hold two pieces of fluid tubing in fluid communication with each other. More particularly, the present invention relates to a connector assembly which prevents accidental disconnection. The present invention is particularly, but not exclusively, useful for lockingly connecting an IV supply line to an IV infusion line in a fluid administration set.

BACKGROUND OF THE INVENTION

Modern medical therapies often incorporate the intravenous ("IV") infusion of fluids into a patient. These fluids, which are often referred to as parenteral fluids, can be used to deliver nutrition as well as medicines to the patient. In fact, many treatments use multiple types of fluids, all of which are to be infused into the patient simultaneously.

To achieve simultaneous infusion of liquids from multiple sources, it is common practice to merge the various fluid supply lines into a single infusion line which is inserted into a patient's vein. In this manner the number of infusion sites are minimized, thereby reducing the ever present risk of infection at an infusion site.

The merger of fluids into a single infusion line is typically achieved by using what is referred to as a Y-site connector assembly. The Y-site connector assembly can be considered as two parts; the Y-site itself and a connector. As the name implies, a Y-site is Y-shaped and has two inputs which are merged into a single output. As can be appreciated, through the use of multiple Y-sites, any number of lines can eventually be merged into a single line. When the merger of fluids is desired, an infusion line is connected to the output of the Y-site and the supply lines providing the fluids to be merged are each connected to one of the Y-site inputs.

Modern Y-site connector assemblies are designed to allow fluid supply lines to be connected and disconnected according to the desired treatment protocols. With the connection and disconnection of lines, not only is there a risk of loosing fluid, there is also the risk of introducing infection producing contaminants. Normally, these risks are minimized by using a contaminant barrier which covers the secondary input to the Y-site when it is not connected to a fluid supply line. These barriers are typically a pierceable seal which covers the Y-site input opening and which are known in the industry as septums. With this type of Y-site, the connector requires a cannula which is able to pierce and/or cross the contaminant barrier.

Another problem which is common for Y-sites is that the connections at the Y-site inputs can accidentally become disconnected. This can, and often does occur when the patient moves and causes tension or pulling on the infusion line. If medical personnel are present when the connection is disconnected, it is possible that reconnection can be easily achieved with minimal disruption in the fluid infusion. On the other hand, if personnel are not present, the disconnected fluid line can go unnoticed for substantial periods of time.

It is desirable to minimize inadvertent disconnection of the lines of an infusion set for several reasons. First, for many patients it is critical that they receive an even and uninterrupted flow rate for the infusion of medicaments. This is extremely critical where the infused medicaments are potentially toxic and need to be controlled. Normally, for such a situation the rate of fluid flow of medicines to the patient must be carefully maintained in a narrow range. Disrupting the steady infusion under these circumstances can in some instances be life threatening because even short disruptions may result in the reduction of the amounts of medicines in the patient to life-threatening levels. Second, many medicaments are extremely expensive, and allowing them to be wasted unnecessarily increases the already high costs of medical treatments.

To prevent the accidental disconnection of the IV supply line at the Y-site, locking Y-site connector assemblies have been developed. For example see U.S. Pat. No. 4,752,292 which is entitled "Medical Connector" and issued to Lopez, et al. A common drawback of the previously known locking connectors such as the device disclosed by Lopez et al., is that they require dedicated features on both the connector as well as the Y-site. This means that unless both the Y-site and the connector have matching interlocking features, the locking mechanism is non-functional. As recognized by the present invention, this lack of functionality can be avoided.

In light of the foregoing, it is an object of the present invention to provide a locking connector assembly for inter-connecting fluid tubes. It is another object of the present invention to provide a locking connector assembly for connecting a fluid supply line to a medical Y-site. It is yet another object of the present invention to provide a connector assembly which includes a locking mechanism on the fluid line connector which is not dependent on a dedicated feature of the Y-site. Still further, it is an object of the present invention to provide a locking connector that is relatively easy to manufacture and is comparatively economical.

SUMMARY OF THE INVENTION

A locking connector assembly for fluid lines is provided by the present invention. The connector assembly of the present invention will be described here in the context of a standard Y-site which can be used in the assembly to merge a primary and a secondary fluid supply line into a single infusion line.

The connector assembly of the present invention generally consists of a fitting, a connector. The fitting is typically a standard Y-site. Such a Y-site is generally Y-shaped and has a lumen which establishes a fluid channel through the Y-site. The Y-site also has a primary input, a secondary input, and an output which are all in fluid communication with the lumen. The primary input of the Y-site is often fixedly attached to a primary supply line by means well known in the art, such as solvent bonding. The secondary input, however, is not initially attached to any fluid line. Instead, the secondary input has a contaminant barrier type septum which is positioned across the opening of the secondary input of the Y-site. A secondary supply line is then connectable to the secondary input of the Y-site via the connector of the present invention.

As is contemplated by the present invention, the connector consists of a shrouded cannula and a retention clip. The shrouded cannula includes a shroud portion which defines a recess. The shrouded cannula also includes a hollow cannula which positioned in the recess with the shroud substantially surrounding the cannula. Further, the shroud portion of the shrouded cannula has an open end which allows access into the recess and which is sized to receive the secondary input of the Y-site of the connector assembly. The other end of the shrouded portion is closed and includes an inlet mouth which interconnects a secondary fluid supply line in fluid communication with the cannula to place the secondary supply line in fluid communication with the cannula in the recess.

The cannula referred to above is fixedly attached to the closed end of the shroud portion such that the first end of the cannula extends into the recess of the shroud and the second end of the cannula is in fluid communication with the inlet mouth of the shroud. The cannula thereby establishes a fluid passageway from the inlet mouth of the shrouded cannula through the recess of the shrouded cannula. With this configuration, the hollow cannula is positioned such that when the secondary input of the Y-site is received by the recess of the shroud, the first end of the cannula extends through the septum covering the secondary input. In this manner, when the connector is installed and the cannula extends through the septum, a continuous fluid passageway is established which extends from the inlet mouth of the shroud of the connector, across the septum and into the lumen of the Y-site.

As noted above, the connector of the present invention includes a retention clip which has a pair of prongs that are separated by a gap. Importantly, the prongs of the retention clip are shaped such that when the secondary input of the Y-site is in the recess of the shroud, the retention clip is engagable with both the shroud of the shrouded cannula and with the Y-site to hold the shrouded cannula in fluid communication with the secondary input of the Y-site. More specifically when engaged with the Y-site, the prongs of the retention clip extend through a pair of slots that are formed through in the shroud to cooperatively engage a protruding structure on the Y-site.

As intended for the present invention, the prongs of the retention clip are designed to cooperatively engage surface irregularities such as protrusions which exist on a typical Y-site. Specifically, when the shrouded connector is properly connected to the Y-site, each prong of the retention clip will be positioned so that the protruding surface irregularity of the Y-site is positioned between the prong and the secondary input of the Y-site. Thus, because there is also cooperative engagement between the prongs of the retention clip and the slots in the shroud, the shrouded cannula will be lockingly held in fluid communication with the secondary input of the Y-site. With this cooperation of structure, the connector is usable with a variety of Y-sites or other fittings, none of which must include a dedicated feature for cooperation with the retention clip of the present invention.

The retention clip of the present invention can be tethered to the shrouded cannula by a tether attached at its first end to the retention clip. The second end of the tether includes a C-clip which is attachable to the shrouded cannula.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF PREFERRED EMBODIMENTS

Figure 1:
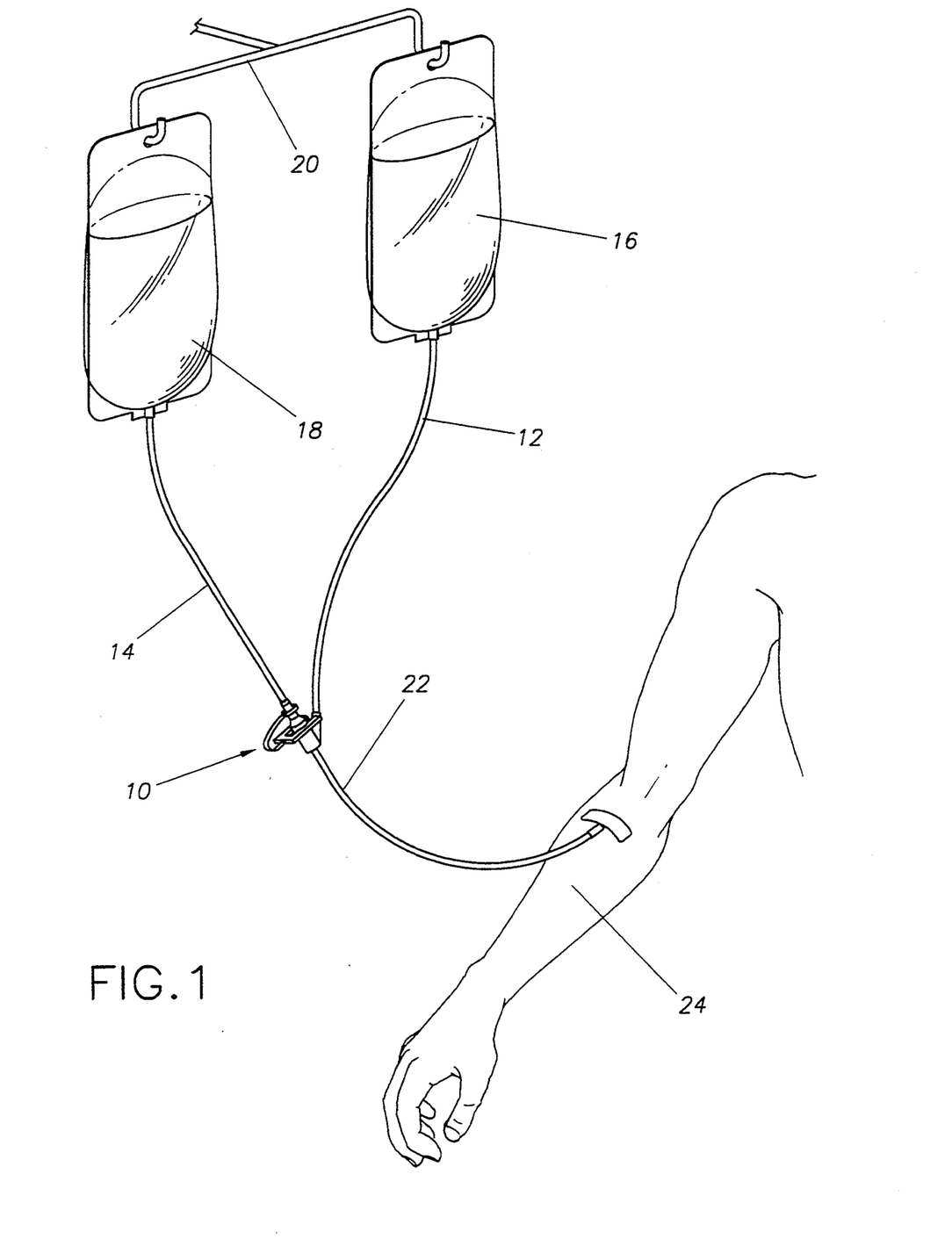
FIG. 1 is a perspective view of the first preferred embodiment of the connector assembly in its intended environment.

Referring initially to FIG. 1, the connector assembly of the present invention is shown and generally designated 10. Connected to connector assembly 10 is a primary supply line 12 and a secondary supply line 14. Supply lines 12 and 14 are connected to a primary I.V. fluid bag 16 and secondary I.V. fluid bag 18, respectively. Each of the two I.V. bags is hung from an I.V. rack 20 as is generally known in the industry. Connected to connector assembly 10 is an infusion line 22 which is inserted into a vein of the patient 24. In this manner, fluids are permitted to flow from I.V. bags 16 and 18 through supply lines 12 and 14 through connector assembly 10 and into infusion line 22 eventually making their way into a vein of patient 24.

The first preferred embodiment of connector assembly 10 is shown in FIGS. 2, 3, 4 and 5. Connector assembly 10 of the first preferred embodiment of the present invention generally consists of Y-site 26 and shrouded connector 28.

The Y-site 26 of the present invention can be of a type as is well known in the art. This kind of Y-site 26 is generally Y-shaped and has a lumen 30. Additionally Y-site 26 has a primary input 32 and secondary input of 34. The fluid passageways of primary input 32 and secondary input 34 of Y-site 26 merge into a single fluid passage way which establishes Y-site output 36.

For purposes of the present invention, Y-site 26 is configured such that fluid flow through the Y-site is in the direction from primary input 32 and secondary input 34 to output 36. Said differently, the primary and secondary inputs 32 and 34 are upstream from the output 36.

The upstream end of primary input 32 is connected to primary supply line 12. Preferably, the connection between primary supply line 12 and primary supply input 32 is a pressure fit. Alternate means of connection such as connectors, gluing, bonding or other means are likewise acceptable without departing from the spirit of the present invention.

The upstream end of secondary input 34 ends at lip 38 which establishes inlet mouth 40. Also at the upstream end of secondary input 34 is a contaminant barrier means which is preferably a pierceable septum 42. Septum 42 is typically made of an elastomeric material, such as rubber. Septum 42 includes an inside skirt 44 and an outside skirt 46 attached to the pierceable portion of the septum 42.

Output 36 of Y-site 26 is connected to infusion line 22 via a fitting similar to that between primary supply line 12 and primary input 32. Several well known methods of connection can be used; solvent bonding is but one example.

Y-site 26 is preferably made of a hard and resilient plastic, although other materials with similar qualities such as glass or composite materials could likewise be used. It is preferable that whatever material is used is substantially transparent, although non-transparent materials could be used.

Figure 2:
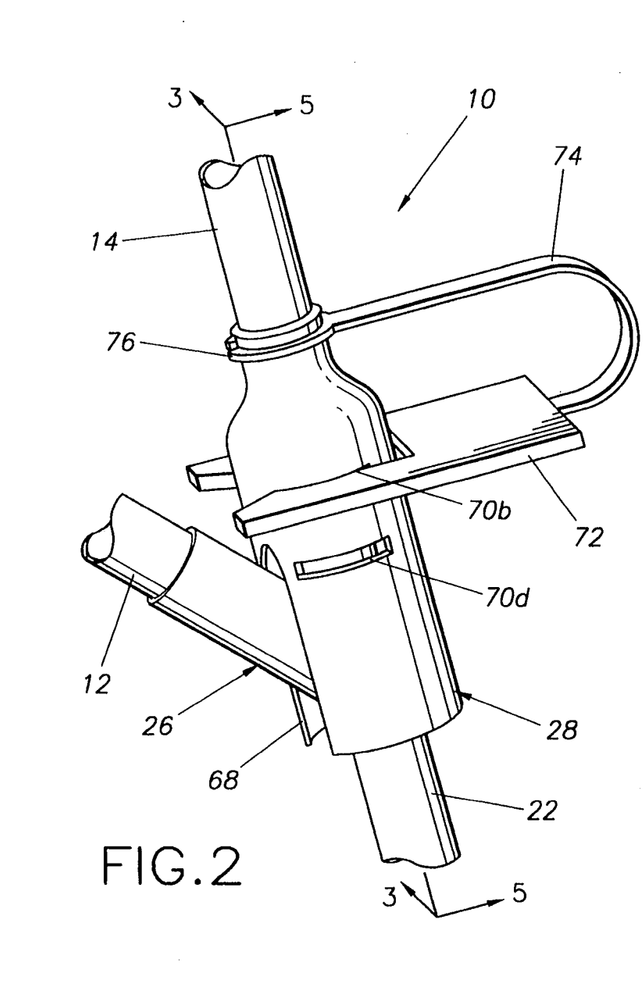
FIG. 2 is an enlarged perspective view of the first preferred embodiment of the connector assembly.
Figure 3:
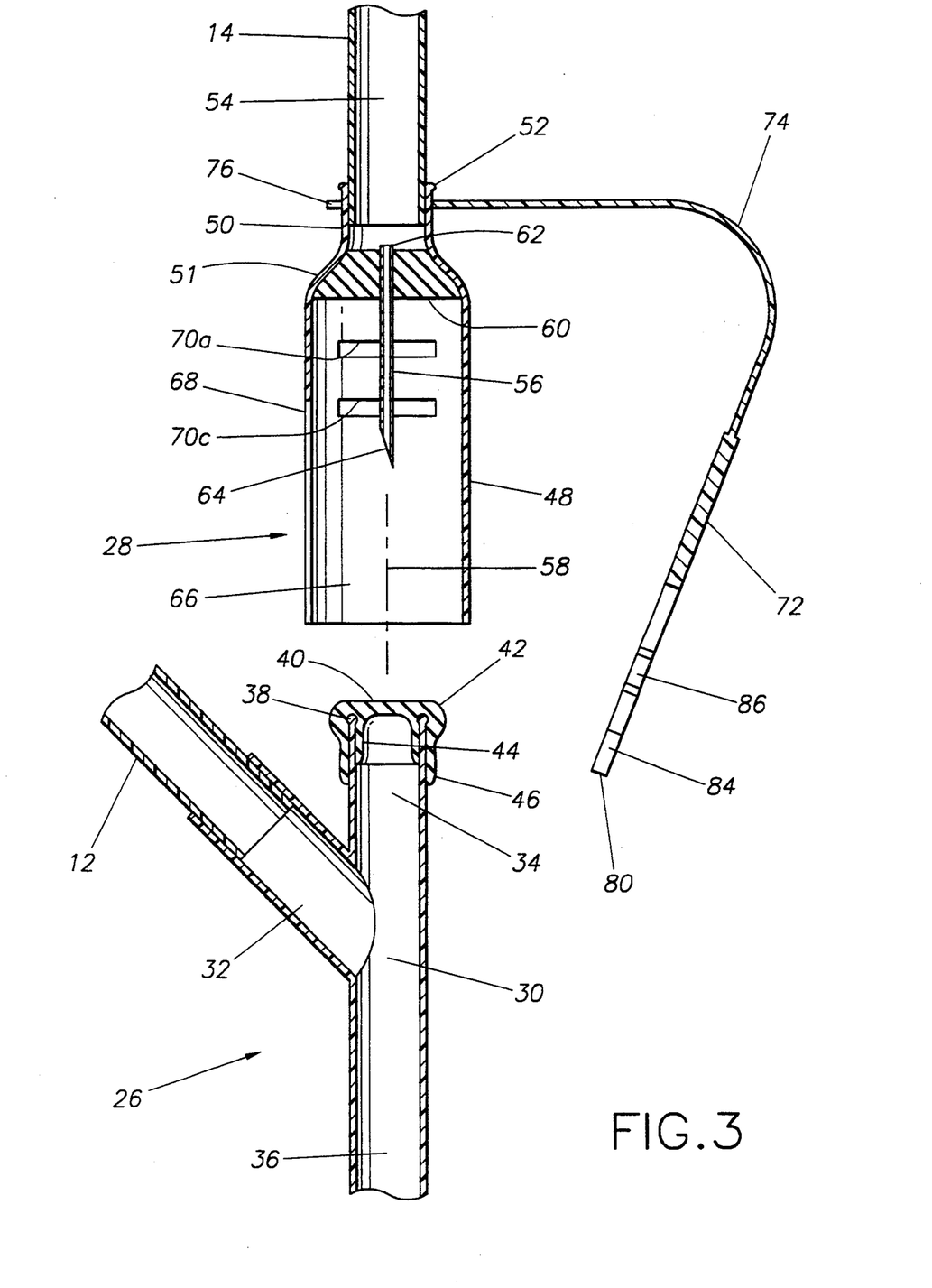
FIG. 3 is a cross-sectional view of the connector assembly as would be seen along the line 3—3 in FIG. 2 if the connector assembly were in its disconnected configuration.

As is perhaps best seen in FIGS. 2 and 3, shrouded connector 28 is a substantially cylindrical shaped hollow member having a body portion 48 and a neck portion 50. Preferably the diameter of the shrouded connector 28 is greater at the body portion than the neck portion thereby establishing a shoulder portion 51.

Neck portion 50 terminates at a lip 52 which establishes inlet mouth 54. Inserted into inlet mouth 54 is secondary supply line 14. The connection between secondary supply line 14 and inlet mouth 54 is preferably a pressure fit although as indicated above, gluing, bonding or other connecting means known in the art is equally acceptable without departing from the spirit and scope of the invention.

A cannula 56 is preferably positioned in the shrouded connector 28 substantially along the longitudinal access 58 of the shrouded connector 28. Cannula 56 is held in position by means of a cannula support 60 which a substantially plug-like member bonded to the interior surface of said shrouded connector 28. Cannula 56 is likewise bonded fixed to said cannula support 60 by means of either a pressure fit or preferably bonding with an adhesive epoxy or similar material. The upstream end 62 of cannula 56 terminates upstream of said cannula support 60. Downstream end 64 of cannula 56 ends in a recess 66 established in the interior of shrouded connector 28. In this manner, a continuous fluid passageway is established from secondary supply line 14 into inlet mouth 54, then into the upstream end of cannula 56 and ending at the downstream end 64.

Downstream end 64 of cannula 56 is preferably a sharpened needle type cannula. Alternatively, it is possible for cannula 56 to be a blunt cannula without departing from the spirit and scope of the present invention. If cannula 56 is blunt, septum 42 is preferably pre-split as is well known in the art.

The body portion 48 of the shrouded connector 28 defines a recess 66 and preferably includes a Y-site slot 68. Y-site slot 68 is positioned and sized to accommodate primary input 32 of Y-site 26 when shrouded connector 28 is connected to Y-site 26.

Additionally, body portion 48 includes one or more lateral slots 70. Slots 70 are through-slots which extend from the exterior surface of body portion 28 into the interior surface of body portion 28, thereby establishing a passageway from the exterior of shrouded connector 28 to the recess 66.

Figure 5:
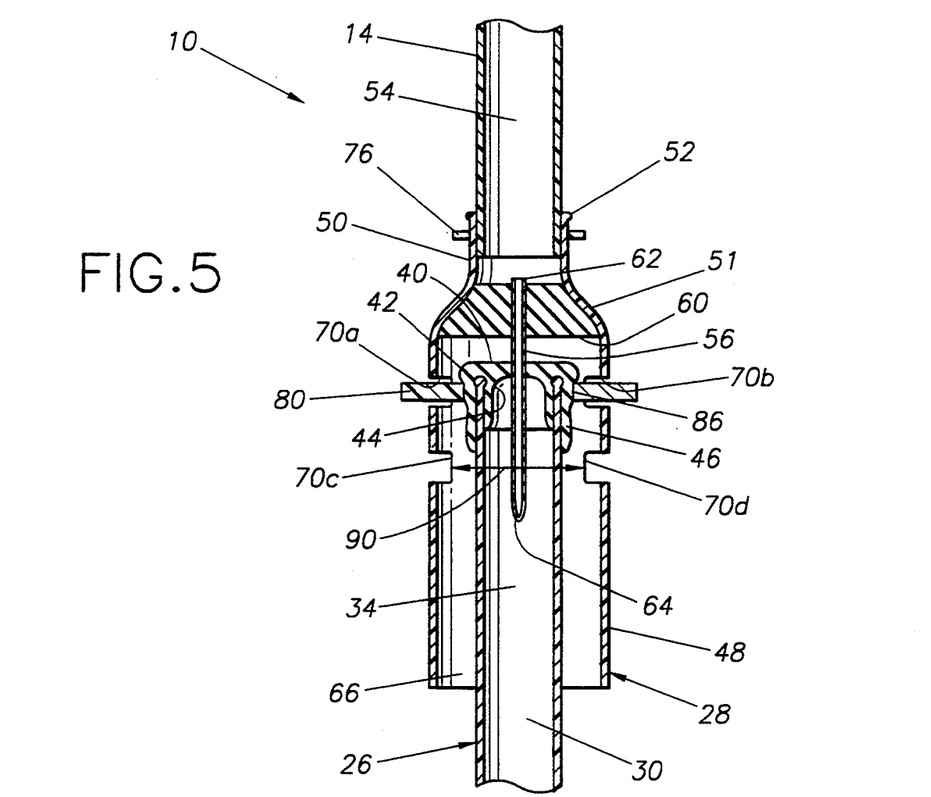
FIG. 5 is a cross-sectional view of the connector assembly in its connected and locked configuration as seen along the line 5—5 in FIG. 2.

As is best seen in FIG. 5, there are preferably two pairs of slots 70 (slots 70a, 70b, 70c and 70d) on opposite sides of shrouded connector 28. The benefit of having slots on opposite sides of the connector will be discussed in greater detail below. The benefit of having multiple pairs of slots is that it allows the shrouded connector 28 to be used with different types of Y-sites and or other types of fittings. The inclusion of multiple pairs of slots 70 allows the user of the connecter assembly 10 to choose the most effective slot for the locking means discussed in detail below.

Figure 6:
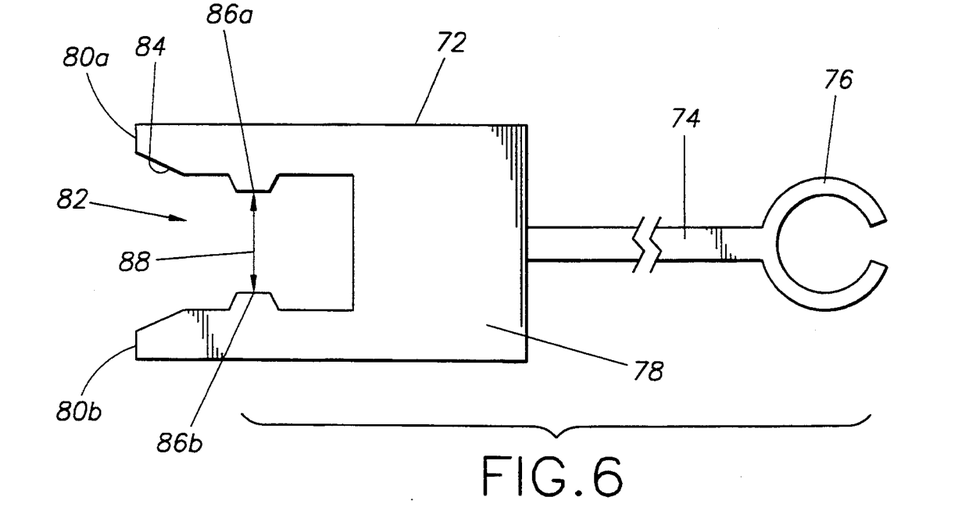
FIG. 6 is a top view of the retention clip of the present invention.

The principle component of the locking means of the present invention is retention clip 72. Preferably, retention clip 72 is attached to neck portion 50 of the shrouded connector 28. While retention clip 72 is shown in other drawings, the details of retention clip 72 are best seen in FIG. 6. Retention clip 72 is connected to a tether 74 which has a C-clip 76 attached at the end of the tether opposite the retention clip. C-clip 76 is sized to cooperatively receive the neck portion 50 of the shrouded connector 28. Preferably, C-clip 76 is removable from neck portion 50.

Alternatively, the tether or the C-clip could be permanently affixed to the neck portion 50 via an adhesive or other bonding means. As those skilled in the art will appreciate, the C-clip, when not permanently affixed to the neck portion, allows rotation of the C-clip about the neck portion 50 as well as longitudinal movement of the C-clip along the neck portion 50 between lip 52 and shoulder portion 51.

Retention clip 72 is a substantially U-shaped member having a base portion 78 and preferably a pair of prongs 80a and 80b. The tips of prongs 80a and 80b are separated leaving a gap 82. Gap 82 is sized to cooperatively receive the shrouded connector 28 along body portion 48. Both prong 80a and 80b have a ramp portion 84 which narrows gap 82 as it progresses further into retention clip 72. Preferably, both prong 80a and 80b are shaped to include a protrusion 86 which is sized to fit within slots 70 of the shrouded connector 28. As those skilled in the art will appreciate, it is possible for the prongs 80a and 80b to be variously shaped to be insertable into slots 70 and may or may not include protrusions 86. If prongs 80 include protrusions 86, it is preferable that distance 88, the distance between opposing protrusions 86a and 86b (see FIG. 6), is slightly less than distance 90, the minimum lateral distance between opposing slots (see FIG. 5). With his configuration prongs 80 need to temporarily bend slightly outward thereby lengthening distance 88 when retention clip 72 is slipped onto shroud 28. In this manner, once installed the retention clip 72 remains selectively lockingly engaged with shroud 28. To remove retention clip 72 from shroud 28, prongs 80 again need to be temporarily bent outward to clear the shroud 28.

To make a locking connection between connector 28 and Y-site 26, the connector 28 is positioned substantially as is shown in FIG. 3. The connector 28 is then moved toward Y-site 26 until cannula 56 contacts septum 42. Continual, increasing pressure is applied on connector 28 in a direction toward Y-site 26 until septum 42 is pierced by cannula 56. Connector 28 is then continually advanced over Y-site 26 such that primary input 32 of Y-site 26 slides into Y-site slot 68. Connector 28 is continually advanced until septum 42 contacts cannula support 60 or primary input 32 contacts the upstream end Y-site 68, whichever is first. Thusly, a continuous fluid passageway is established beginning with secondary supply line 14 through cannula 56 and into lumen 30 of Y-site 26.

Figure 4:
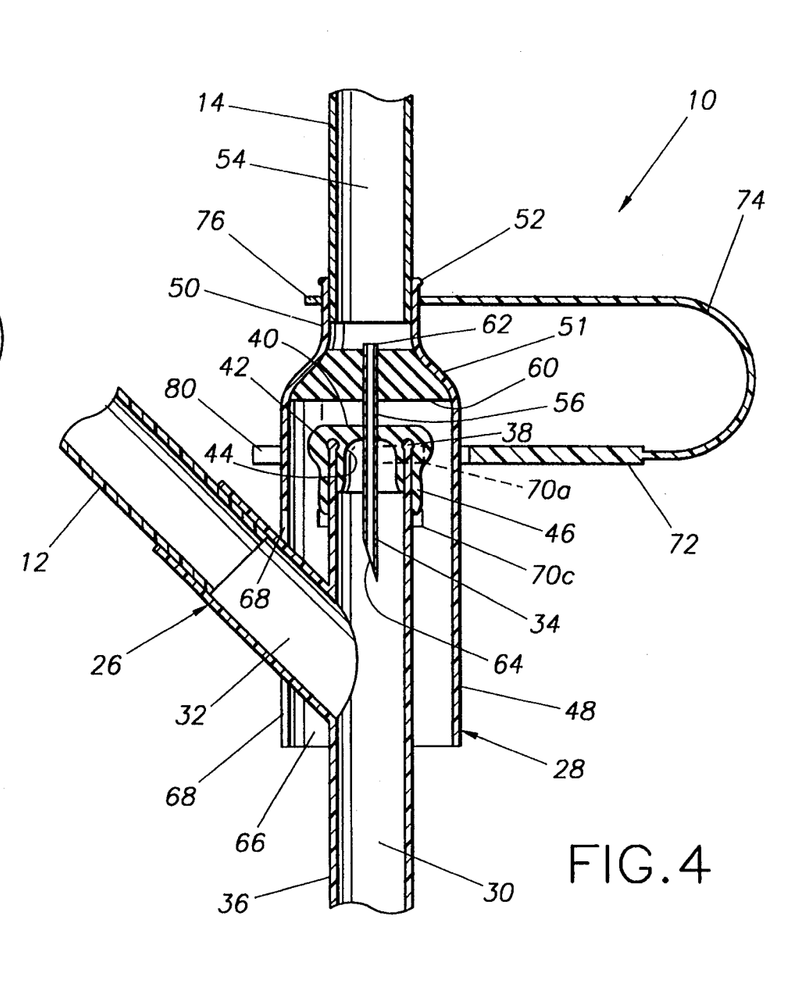
FIG. 4 is a cross-sectional view of the connector assembly in its connected and locked configuration as seen along the line 3—3 in FIG. 2.

At that point, the shrouded connector 28 is not lockingly attached to Y-site 26. To accomplish the locking connection, retention clip 72 must be placed into the locking configuration. To do this, the shrouded connector 28 is placed into gap 82 of retention clip 72. The retention clip 72 is maintained substantially perpendicular to the longitudinal access of shrouded connector 28. Moreover, retention clip 72 is positioned along the body portion 48 such that it is adjacent a pair of slots 70 in said body portion 48. Retention clip 72 is advanced laterally across shrouded connector 28 until protrusions 86 of prongs 80 slide into slots 70 in the shrouded connector 28 and engage a portion of Y-site 26. The locking configuration is best seen in FIGS. 4 and 5 which are views at 90 degrees relative to each other. As is best seen in FIG. 5, protrusions 86 preferably engage the outer skirt 46 of septum 42 slightly downstream from the lip 38 of the inlet mouth 40. As will be appreciated as those skilled in the art, the outside diameter of the septum is slightly greater at the lip 38 than it is slightly downstream. In this manner prongs 86 engage along the portion where the diameter of the Y-site (including the septum) is slightly less. In this manner, the prongs 86 are prevented from moving upstream along septum 42 because of the increase of the Y-site diameter at that point. Because prongs 86 are extending into shrouded connector 28 and are cooperatively engaging shrouded connector 28, shrouded connector 28 likewise cannot be move longitudinally relative to the Y-site 26 once the retention clip is installed as shown in FIGS. 4 and 5. As those skilled in the art will appreciate the prongs 80 are sized and shaped such that prongs 80 slightly compress the outside skirt 46 of septum 42 when the prongs 80 engage the outside skirt 46.

One particular benefit of the present invention is that it allows use of shrouded connector with different types of Y-sites. It accomplishes this by the use of the slots 70 in cooperation with prongs 80 to engage a surface irregularity on the Y-site 26. While the preferred embodiment described above engages a surface irregularity on the septum 42 of the Y-site 26, those skilled in the art will appreciate that any surface irregularity along the Y-site could be utilized merely by adjusting the location of the slots 70.

Figure 7:
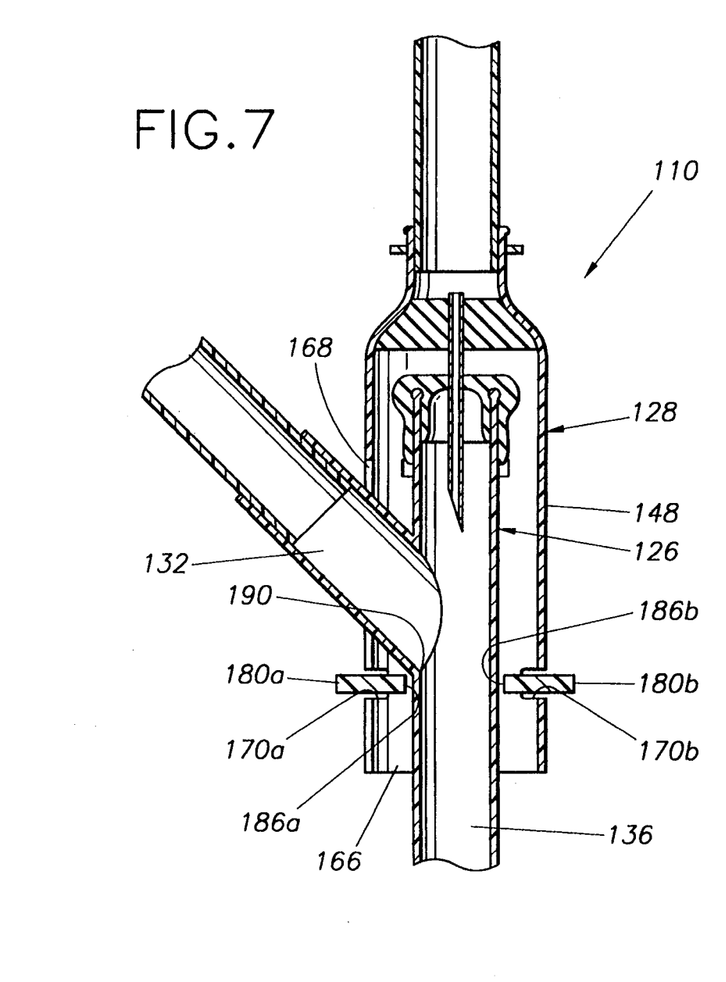
FIG. 7 is a cross-sectional view of the second preferred embodiment of the connector assembly of the present invention.

For example, referring to FIG. 7, an alternative embodiment 110 is shown. Alternative embodiment 110 includes a shrouded connector 128 which receives a common Y-site 126. In this embodiment, those skilled in the art will appreciate that slots 170 (which are substantially equivalent to the slots 70 shown in the previous embodiment) are located substantially more downstream along the body portion 148 of the shrouded connector 128. In this manner, once prongs 180a and 180b are on opposites sides of shrouded connector 128 such that protrusions 186a and 186b extend into the recess 166 of the shrouded connector 128, the device is again in a substantially locked configuration.

In this embodiment, the locking engagement is achieved by protrusions 186a and 186b being at a location downstream from input-output interface 190 where primary input 132 connects to the output 136 of Y-site 126. Moving the connector 128 away from Y-site 126 is prevented by engagement between protrusions 186a and the input-output interface 190. Those skilled in the art will appreciate that the contact between protrusions 186a and interface 190 is required because the shrouded connector 128 cannot be rotated relative to the Y-site 126. This rotational movement is prevented because primary input 132 is positioned in Y-site slot 168 of the shrouded connector 28. If the shrouded connector 128 is attempted to be rotated relative to the Y-site 126, the primary input 132 would contact the edge of the Y-site slot 168 thereby preventing relative rotation.

In light of the foregoing preferred embodiments, those skilled in the art will appreciate that other types of Y-sites or other fittings which have a surface irregularity could be used with the connector of the present invention as long as the retention clip can be inserted into slots which are downstream from the surface irregularity where the surface irregularity makes the Y-site or other fitting have an increasing diameter as experienced by the retention clip as it is moved upstream along Y-site or other connector.

As will be appreciated by those skilled in the art, an infusion fitting, other than a Y-site fitting, such as a tubular fitting having a septum placed over its input, would be equally useable with the present invention. An exemplary arrangement is shown in FIG. 8.

Figure 8:
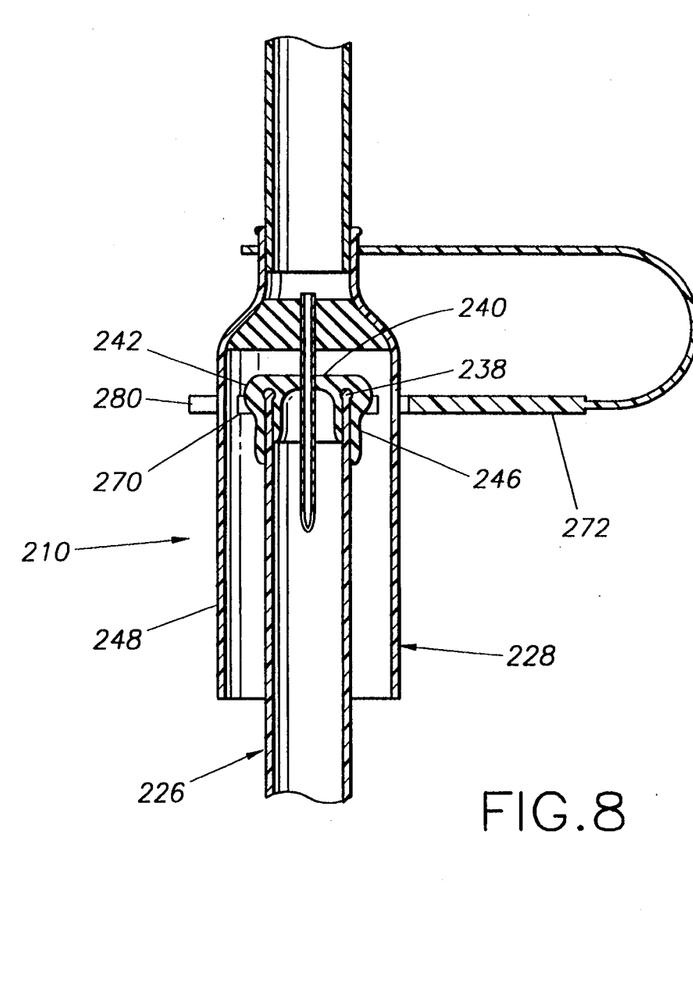
FIG. 8 is a cross-sectional view of the third preferred embodiment of the connector assembly of the present invention.

In FIG. 8 an alternative embodiment 210 of the present invention is shown. As will be appreciated, the shrouded connector and retention clip are substantially equal to those shown in FIGS. 2 through 7 except that the body portion 148 does not include a Y-site slot because the connector 226 does not include any members extending radially which must be accommodated by the shrouded connector 228. In the embodiment shown in FIG. 8, the tubular fitting 226 ends at its upstream end at a lip 238 which establishes an inlet mouth 240. Inlet mouth 240 is covered by pierceable septum 242 substantially in a manner similar to that shown for the Y-site in FIG. 3. As those skilled in the art will appreciate, the locking mechanism of the embodiment shown in FIG. 8 is substantially equivalent to locking mechanism shown in FIGS. 2 through 6. As in shown in FIG. 8, the retention clip 272 includes prongs 280 which are shaped to fit on either side of the shrouded connector 228 and into slots 270. Prongs 280 are formed to engage the outer skirt of the pierceable septum slightly downstream from the lip 238. Again, in this manner, once the retention clip is installed substantially as is shown in FIG. 8, the shrouded connector 228 is prevented from moving in a direction away from the connector 226.

While the particular Locking Connector Assembly as herein shown and disclosed in detail is fully capable of obtaining the objects and providing the advantages herein before stated, it is to be understood that it is are merely illustrative of the presently preferred embodiments of the invention and that no limitations are intended to the details of construction or design herein shown other than as described in the appended claims.

I claim:

1. A shrouded cannula for connecting a fluid supply line to an infusion line, the infusion line having a septum mounted thereon and an external skirt extending outwardly and radially therefrom, said shrouded cannula comprising:

a substantially cylindrical shroud, said shroud having a longitudinal axis, an inlet portion connectable to said supply line, and a receiving portion having an inner surface and an outer surface, said inner surface defining a recess to receive said infusion line;

at least one lateral slot formed circumferentially in said shroud, said slot extending from said outer surface to said inner surface and through said shroud;

a cannula completely surrounded by said shroud and attached thereto to be located in said recess and positioned to pierce said septum on said infusion line to establish fluid communication with said supply line; and a locking mechanism selectively insertable through said slot, and held therein for abutting said skirt of said infusion line, when said infusion line is located in said recess to prevent said infusion line from exiting said recess.

2. The shrouded cannula as recited in claim 1 wherein said shroud is formed with a least one pair of lateral through slots and wherein said locking mechanism comprises a substantially U-shaped retention clip, said retention clip having a pair of prongs separated by a gap sized to receive said shroud between said prongs, each said prong engagable with said skirt of said infusion line through one of said slots.

3. The shrouded cannula as recited in claim 2 wherein each of said prongs includes a protrusion for engaging said infusion line.

4. The shrouded cannula as recited in claim 3 wherein said protrusion is shaped to selectively engage a surface irregularity on said infusion line.

5. The shrouded cannula as recited in claim 2 wherein said retention clip includes a tether attachable to said shroud.

6. The shrouded cannula as recited in claim 5 wherein said tether includes a C-clip attachable to said inlet portion of said shroud.

7. The shrouded cannula as recited in claim 2 wherein each slot of said at least one pair of slots is on opposite sides of said shroud.

8. The shrouded cannula as recited in claim 1 wherein said inlet portion includes a mouth which is connectable to said fluid supply line, said recess having a recess diameter and said inlet mouth having an inlet mouth diameter which is less than said recess diameter.

9. The shrouded cannula as recited in claim 1 wherein said cannula is a sharpened needle substantially along the longitudinal axis of said shroud.

10. The shrouded cannula as recited in claim 1 wherein said cannula is a blunt cannula substantially along the longitudinal axis of said shroud.

11. A device for connecting a fluid supply tube in fluid communication with a fluid infusion tube, the infusion tube having an external protrusion and a pierceable septum across an inlet of the infusion tube, the device comprising:

a cannula having a first end and a second end, said first end of said cannula being attachable in fluid communication with said supply line and said second end of said cannula being positioned to pierce said septum and establish fluid communication between said supply tube and said infusion tube;

a shroud having a first end and a second end with a recess formed therebetween, said first end of said shroud being attached to said first end of said cannula to completely surround said cannula and to position said cannula in said recess, said second end of said shroud being open to receive said inlet of said infusion tube in said recess as said cannula pierces said septum, and said shroud being formed with at least one slot circumferentially formed therethrough; and a retention clip formed with a prong, said prong being partially insertable through said slot in said shroud to abut said protrusion on said infusion tube and position said prong between said slot in said shroud and said protrusion of said infusion tube to hold said cannula in said septum.

12. The device as recited in claim 11 wherein said retention clip is rotatably connected to said first end of said shroud.

13. The device as recited in claim 12 wherein said at least one slot comprises a pair of slots, each one of said pair of slots being positioned on opposite sides of said shroud.

14. The device as recited in claim 13 wherein said shroud has a longitudinal axis and said cannula is a sharpened needle substantially along the longitudinal axis of said shroud and said septum is pierceable by said needle.

15. The device as recited in claim 13 wherein said shroud has a longitudinal axis and said cannula is a blunt cannula substantially along the longitudinal axis of said shroud, said septum being penetrable by said blunt cannula.

16. An IV fluid tube connection assembly, said assembly comprising:

a Y-site connector having a primary input, a secondary input and an output;

a primary supply line connected to said primary input of said Y-site;

an infusion line connected to said output of said Y-site;

a seal attached to said secondary input for sealing said secondary input of said Y-site, an external skirt extending outwardly and radially from said secondary input;

a secondary supply line;

a substantially cylindrical shroud connected to said secondary supply line, said shroud having a longitudinal axis, an inlet portion connected to said secondary supply line, a receiving portion having an inner surface and an outer surface, said inner surface defining a recess sized to receive said secondary input of said Y-site;

at least one pair of lateral slots circumferentially formed in said shroud, each said slot extending from said outer surface and through said shroud to said inner surface of said shroud to allow access to said Y-site through said shroud when said secondary input of said Y-site is in said recess;

a cannula for piercing said seal, said cannula being completely surrounded by said shroud and attached thereto to be located in said recess, said cannula establishing a fluid passageway to said secondary supply line through said seal when said secondary input of said Y-site is in said recess; and a locking mechanism selectively insertable through said pair of slots and held therein for abutting said skirt when said secondary input is located in said recess to prevent said secondary input from exiting said recess.

17. The connection assembly as recited in claim 16 wherein said locking mechanism comprises a substantially U-shaped retention clip, said retention clip having a pair of prongs separated by a gap sized to receive said shroud between said prongs, each said prong being engagable with said Y-site through one of said slots.

18. The connection assembly as recited in claim 17 wherein each of said prongs includes a protrusion for engaging a surface irregularity on said Y-site.

19. The connector assembly as recited in claim 18 wherein said seal on said Y-site forms said external skirt and wherein each said protrusion is shaped to selectively engage and compress said external skirt portion of said seal.

20. The connection assembly as recited in claim 18 wherein said slots in said shroud are positioned such that each said protrusion will selectively engage the Y-site downstream of the intersection between the primary input and the secondary input of the Y-site.

21. The connection assembly as recited in claim 17 wherein said retention clip includes a tether attachable to said shroud, said tether including a C-clip attachable to said inlet portion of said shroud.

22. The connection assembly as recited in claim 17 wherein said cannula is a blunt cannula substantially along the longitudinal axis of said shroud and said seal is penetrable by said blunt cannula.

23. The connection assembly as recited in claim 16 wherein said cannula is a sharpened needle substantially along the longitudinal axis of said shroud and said seal is a septum pierceable by said needle.

* * * * *